US00PP08006P

United States Patent [19]

Hofmann

[11] Patent Number: Plant 8,006

[45] Date of Patent: Oct. 13, 1992

[54] VARIETY OF GERANIUM NAMED MELODY

[75] Inventor: Christa Hofmann, Dresden, Fed. Rep. of Germany

[73] Assignee: Oglevee Ltd., Connellsville, Pa.

[21] Appl. No.: 690,094

[22] Filed: Apr. 23, 1991

[51] Int. Cl.[5] ..... A01H 5/00
[52] U.S. Cl. ..... Plt./87.12
[58] Field of Search ..... Plt./68, 87.12

[56] References Cited

U.S. PATENT DOCUMENTS

P.P. 6,654 3/1989 Craig et al. ..... Plt. 68

*Primary Examiner*—Howard J. Locker
*Attorney, Agent, or Firm*—Webb, Burden, Ziesenheim & Webb

[57] ABSTRACT

The new cultivar is characterized by its hardy, uniquely colored clear pink and accented blooms. It is further characterized by its neat, compact habit. The variety does equally well as a pot plant or a stock plant for cutting production.

1 Drawing Sheet

BACKGROUND OF THE INVENTION

The present invention comprises a new and distinct cultivar of *Pelargonium*×*hortorum* known by the varietal name melody (V.E.B. Code P-55 Oglevee Code 7018). The new variety was discovered in a selected breeding program in 1985 in Berlin, East Germany. The new variety is a selection from the crossing of PAC Yvonne, PAC Laura and blue-rose colored breeding stocks. The new variety was first asexually reproduced by cuttings at VEB Saat-und Pflanzgut, Ex-Und Import in Moosdorfstrabe 3, 1193 Berlin, East Germany. The new variety has been asexually reproduced by cuttings at Oglevee Ltd. in Connellsville, Penn. over a several year period. It has also been trial and field tested at Connellsville and has been found to retain its distinctive characteristics through successive propagations.

The cultivar when grown in a glass greenhouse in Connellsville, Penn. using natural light and 60° F. night, 68° F. and 71° F. vent, has a response time of six weeks from a rooted cutting to flowering in a 10 cm. pot. The response time was determined on plants grown in soilless media employing constant fertilizer 200 parts per million of nitrogen and potassium in full light. The rooted cuttings were potted Feb. 14, 1990 and flowered on Apr. 1, 1990.

DESCRIPTION OF THE DRAWING

The accompanying photographic drawing illustrates the new cultivar, with the colors shown being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Penn. The plant history was taken on six week plants blossomed under natural light in a greenhouse and the color readings were taken indoors under 50–75 foot candles of florescent cool white light. Color references are primarily to the R.H.S. Colour Chart of The Royal Horticultural Society of London.

THE PLANT

Classification:
- *Botanical.*—*Pelargonium*×*hortorum.*
- *Commercial.*—Zonal Geranium.

Form: Compact mound shape, upright.
- *Height.*—18.0 to 20.0 cm. from media surface.
- *Growth.*—Compact mount habit, basal branching, free and early flowering.

Strength: Stands upright without artificial support.

Foliage: Little or no zoning present; stalked leaf attachment.

Leaves:
- *Size.*—8.5 to 9.0 cm. across.
- *Shape.*—Reniform, cordate base.
- *Margin.*—Crenate.
- *Texture.*—Pubescent, dull — not reflective.
- *Color.*—Top: Green group 137B. Bottom: Yellow/green group 146B.
- *Ribs and veins.*—Palmate venation. Color: Yellow/green group 146D.

Petioles:
- *Color.*—Yellow/green group 146B.
- *Length.*—6.5 to 8.0 cm. length.

Stem:
- *Color.*—Yellow/green group 146B.
- *Internodes.*—1.0 to 3.0 cm. in length.

THE BUD

Shape: Hemispherical cluster.

Size: 2.0 to 4.0 cm. across at the widest point.

INFLORESCENCE

Blooming habit: Upright; semi-double and continuous blooming.

Size: 7.0 to 10.5 cm. across.

Borne: Umbel; 4.0 to 7.0 cm. above foliage canopy; florets on pedicel, pedicel on peduncle.

Florets:
- *Form.*—Flat to slightly cupped.
- *Color.*—Top: Upper two petals: Red/purple group 62A with a white eye and veining of Red/purple group 61C. Lower three petals: Red/purple group 62A with a dark eye of Red group 52A. Bottom: Red/purple group 62C.

*Petals.*—5 in number; obovate, separate, not united; margin entire; smooth; flat to slightly cupped.

*Size.*—4.0 to 4.5 cm. across.

*Texture and appearance.*—Smooth, satiny. Color from a distance appears a bright clear pink with an eye of white and accent eyes of a deeper pink.

Petaloids:

*Quantity.*—2-3.

*Shape.*—Petal-like but twisted and deformed.

*Color.*—Top: Red/purple group 62A. Bottom: Red/purple group 62C.

Pedicel:

*Length.*—2.0 to 3.5 cm.

*Color.*—Greyed/purple group 184B.

Peduncle: Arises from the node opposite the leaf petiole.

*Length.*—14.5 to 16.5 cm.

*Color.*—Yellow/green group 146B.

Disease resistance: Not known.

Lasting quality: The open bloom holds together very well even when subjected to heat, wind and rain blooming continuously.

REPRODUCTIVE ORGANS

Stamens:

*Anthers.*—2.0 to 3.0 mm. in length.

*Filaments.*—6.0 to 7.0 mm. in length, white, flat.

*Pollen.*—Golden brown.

Pistils:

*Number.*—One.

*Length.*—9.0 to 10.0 mm.

*Stigma.*—1; 5 parted; red-purple in color.

*Style.*—3.0 to 4.0 mm. in length; red-purple in color.

Ovaries: Superior; pale green; pubescent; 5.0 to 6.0 mm. in length; 2.0 to 3.0 mm. across.

Fruit: None observed.

I claim:

1. A new and distinct variety of Geranium plant, substantially as shown and described.

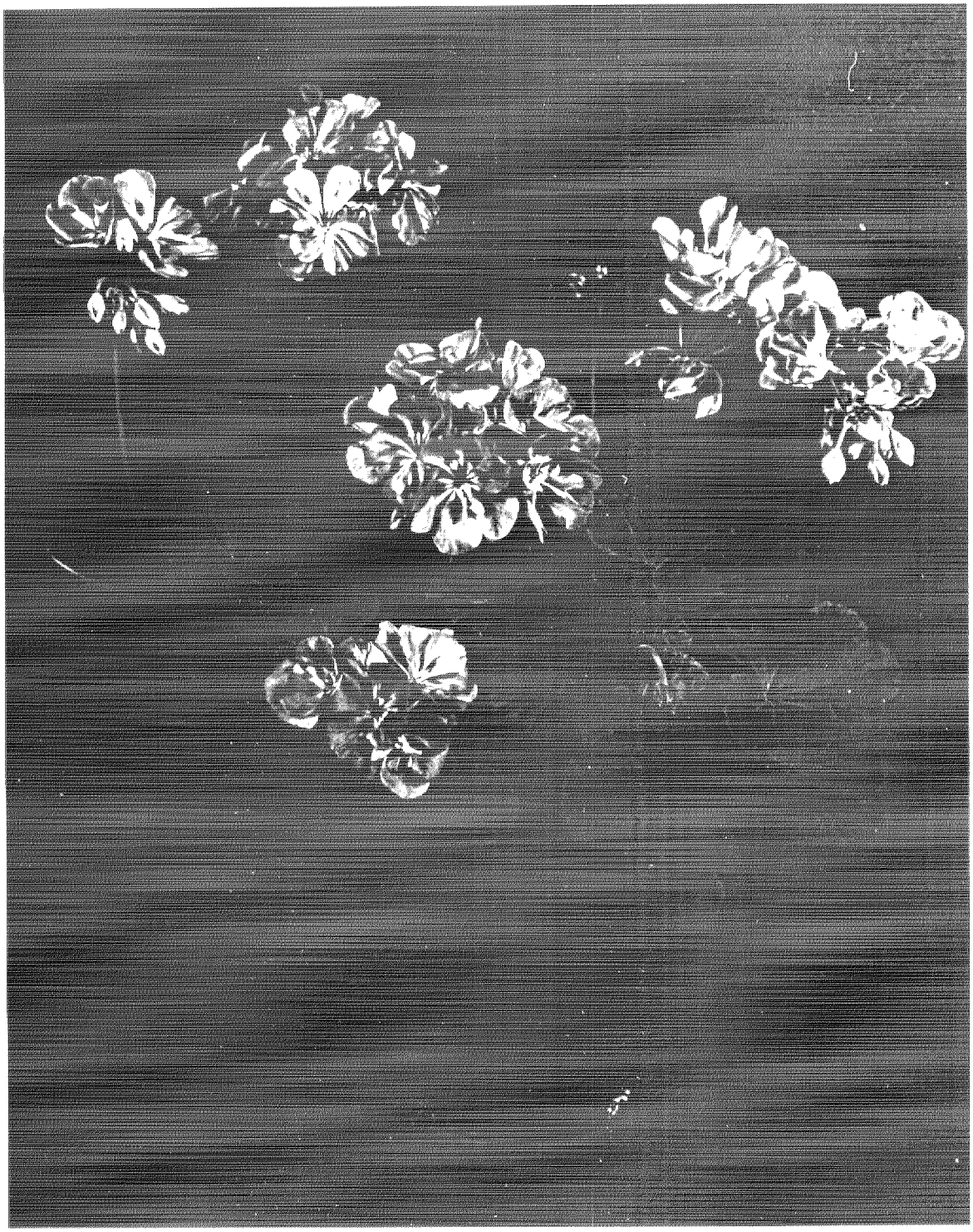

* * * * *